US011110183B2

(12) United States Patent
Mohapatra et al.

(10) Patent No.: US 11,110,183 B2
(45) Date of Patent: Sep. 7, 2021

(54) METHOD OF DELIVERING GENES AND DRUGS TO A POSTERIOR SEGMENT OF AN EYE

(71) Applicants: Shyam S. Mohapatra, Lutz, FL (US); Subhra Mohapatra, Lutz, FL (US); Eleni Markousta, Tampa, FL (US)

(72) Inventors: Shyam S. Mohapatra, Lutz, FL (US); Subhra Mohapatra, Lutz, FL (US); Eleni Markousta, Tampa, FL (US)

(73) Assignees: University of South Florida, Tampa, FL (US); The United States Government as Represented by the Department of Veterans Affairs, Washington, DC (US)

( * ) Notice: Subject to any disclaimer, the term of this patent is extended or adjusted under 35 U.S.C. 154(b) by 184 days.

(21) Appl. No.: 16/531,734

(22) Filed: Aug. 5, 2019

(65) Prior Publication Data

US 2020/0061207 A1 Feb. 27, 2020

Related U.S. Application Data

(60) Provisional application No. 62/714,524, filed on Aug. 3, 2018.

(51) Int. Cl.
| | | |
|---|---|---|
| *C07H 21/04* | (2006.01) | |
| *A61K 47/69* | (2017.01) | |
| *A61K 47/60* | (2017.01) | |
| *A61P 27/02* | (2006.01) | |
| *A61K 9/00* | (2006.01) | |
| *C12N 15/113* | (2010.01) | |
| *A61K 31/7088* | (2006.01) | |
| *A61K 31/4439* | (2006.01) | |
| *A61K 47/61* | (2017.01) | |
| *A61K 47/62* | (2017.01) | |
| *A61K 47/54* | (2017.01) | |

(52) U.S. Cl.
CPC ........ *A61K 47/6935* (2017.08); *A61K 9/0048* (2013.01); *A61K 31/4439* (2013.01); *A61K 31/7088* (2013.01); *A61K 47/549* (2017.08); *A61K 47/60* (2017.08); *A61K 47/61* (2017.08); *A61K 47/62* (2017.08); *A61K 47/6951* (2017.08); *A61P 27/02* (2018.01); *C12N 15/113* (2013.01); *C12N 2310/122* (2013.01); *C12N 2310/14* (2013.01); *C12N 2310/351* (2013.01); *C12N 2310/531* (2013.01); *C12N 2320/31* (2013.01); *C12N 2320/32* (2013.01)

(58) Field of Classification Search
CPC ........................ C12N 15/113; C12N 2310/531
See application file for complete search history.

(56) References Cited

U.S. PATENT DOCUMENTS

2017/0042829 A1* 2/2017 Mao ..................... A61K 47/61

FOREIGN PATENT DOCUMENTS

| CA | 2803446 A1 * | 1/2012 | ........... C12N 15/113 |
| WO | WO 2011/135724 A1 * | 3/2011 | ........... C12N 15/113 |
| WO | WO 2012/024396 A2 * | 2/2012 | ........... C12N 15/113 |
| WO | WO 2017/123996 A1 * | 7/2017 | ........... C12N 15/113 |

OTHER PUBLICATIONS

Paddison et al. (Genes & Development, 16, 948-958, 2002).*
Tam et al. (2010, Protection of Photoreceptors in a Mouse Model of RP10. In: Anderson R., Hollyfield J., LaVail M. (eds) Retinal Degenerative Diseases. Advances in Experimental Medicine and Biology, vol. 664. Springer, New York, NY, pp. 559-565).*
Nam et al. (Journal of Controlled Release, 209, 2015, 179-185).*
Jiang S. et al., Nanotechnology in retinal drug delivery, International Journal of Ophthalmology, 2018; 11(6):1038-1044.
Davies N.M. Biopharmaceutical considerations in topical ocular drug delivery. Clin Exp Pharmacol Physiol. 2000;27(7):558-62.
Ilka R., et al. Nanogel-based natural polymers as smart carriers for the controlled delivery of Timolol Maleate through the cornea for glaucoma. International journal of biological macromolecules. 2018;109:955-62.
Lajunen T., et al. Light activated liposomes: Functionality and prospects in ocular drug delivery. Journal of controlled release : official journal of the Controlled Release Society. 2016;244(Pt B):157-66.
Holden C.A., et al. Polyamidoamine dendrimer hydrogel for enhanced delivery of antiglaucoma drugs. Nanomedicine : nanotechnology, biology, and medicine. 2012;8(5):776-83.
Sahoo S.K., et al. Nanotechnology in ocular drug delivery. Drug Discov Today. 2008;13(3-4):144-51.
Motwani S.K., et al. Chitosan-sodium alginate nanoparticles as submicroscopic reservoirs for ocular delivery: formulation, optimisation and in vitro characterisation. Eur J Pharm Biopharm. 2008;68(3):513-25.
Kutlehria S., et al. Tacrolimus Loaded PEG-Cholecalciferol Based Micelles for Treatment of Ocular Inflammation. Pharmaceutical research. 2018;35(6):117.
Sharma A., et al. Epigenetic Modification Prevents Excessive Wound Healing and Scar Formation After Glaucoma Filtration Surgery. Invest Ophthalmol Vis Sci. 2016;57(7):3381-9.
Tandon A., et al. BMP7 gene transfer via gold nanoparticles into stioma inhibits corneal fibrosis in vivo. PloS one. 2013;8(6):e66434.
Palmerston Mendes L., et al. Dendrimers as Nanocarriers for Nucleic Acid and Drug Delivery in Cancer Therapy. Molecules. 2017;22(9).

(Continued)

*Primary Examiner* — Amy H Bowman
(74) *Attorney, Agent, or Firm* — Michele L. Lawson; Smith & Hopen, P.A.

(57) ABSTRACT

A multifunctional dendrimer nanoparticle and method of treating diseases of the posterior segment of the eye is presented. The functionalized polyamidoamine (PAMAM) dendrimer effectively delivers drugs and/or genes to the posterior eye, thereby providing for the effective, non-invasive, and topical treatment of diseased in the posterior eye. The multifunctional dendrimer nanoparticle has shRNA-encoding DNA and small molecule drug encapsulated cyclodextrin complexed to the outer surface of the dendrimer for delivery to the posterior segment of the eye.

6 Claims, 7 Drawing Sheets

(56) References Cited

OTHER PUBLICATIONS

Somani S., et al.Transferrin-bearing polypropylenimine dendrimer for targeted gene delivery to the brain. Journal of controlled release : official journal of the Controlled Release Society. 2014;188:78-86.

Biswas S., and Torchilin V.P. Dendrimers for siRNA Delivery. Pharmaceuticals (Basel). 2013;6(2):161-83.

Soto-Castro D., et al. Solubilization and anticancer-activity enhancement of Methotrexate by novel dendrimeric nanodevices synthesized in one-step reaction. Bioorg Chem. 2012;41-42:13-21.

Duncan R., and Izzo L. Dendrimer biocompatibility and toxicity. Advanced drug delivery reviews. 2005;57(15):2215-37.

Pescina S., et al. Cell penetrating peptides in ocular drug delivery: State of the art. Journal of controlled release official journal of the Controlled Release Society. 2018;284:84-102.

Tai L., et al. A novel penetratin-modified complex for noninvasive intraocular delivery of antisense oligonucleotides. Int J Pharm. 2017;529(1-2):347-56.

Tai L., et al. Noninvasive delivery of oligonucleotide by penetratin-modified polyplexes to inhibit protein expression of intraocular tumor. Nanomedicine : nanotechnology, biology, and medicine. 2017;13(6):2091-100.

Liu C., et al. Facile Noninvasive Retinal Gene Delivery Enabled by Penetratin. ACS Appl Mater Interfaces. 2016;8(30):19256-67.

Puglia C., et al. Lipid nanocarriers (LNC) and their applications in ocular drug delivery. Curr Med Chem. 2015;22(13):1589-602.

Attama A.A et al. Sustained release and permeation of timolol from surface-modified solid lipid nanoparticles through bioengineered human cornea. Curr Eye Res. 2009;34(8):698-705.

Kadam R.S., et al. Suprachoroidal delivery in a rabbit ex vivo eye model: influence of drug properties, regional differences in delivery, and comparison with intravitreal and intracameral routes. Mol Vis. 2013;19:1198-210.

\* cited by examiner

PAMAM Dendrimer G4-NH2

METHOD OF DELIVERING GENES AND DRUGS TO A POSTERIOR SEGMENT OF AN EYE

CROSS REFERENCE TO RELATED APPLICATIONS

This application is a nonprovisional of and claims priority to U.S. Provisional Patent Application Ser. No. 62/714,524, entitled "Method of Delivering Genes and Drugs to a Posterior Segment of an Eye", filed Aug. 3, 2018, the contents of which are hereby incorporated by reference into this disclosure.

GOVERNMENT SUPPORT STATEMENT

This invention was made with government support under Grant Nos. BX002668 and BX003685 awarded by the Department of Veterans Affairs. The government has certain rights in the invention.

FIELD OF INVENTION

This invention relates, generally, to gene and drug delivery to a specific location in a body. More specifically, it relates to methods and compositions to deliver genes and drugs to a posterior segment of an eye.

BACKGROUND OF THE INVENTION

A report from the Center for Disease Control (CDC) estimates that more than 3.3 million people in the US, aged 40 or older, are either legally blind or have poor vision. Age-related macular degeneration (AMD) is the leading cause of permanent vision impairment among those aged 65 or older while diabetic retinopathy (DR) is the leading cause of blindness in young to middle aged individuals. (Jiang S. et al., Nanotechnology in retinal drug delivery, International Journal of Ophthalmology, 2018; 11(6):1038-1044).

The easiest way to deliver therapeutics to the eye is through topical administration, mostly in the form of eye drops; however, the effectiveness of this method for retinal gene delivery is limited. (Davies N M. Biopharmaceutical considerations in topical ocular drug delivery. Clin Exp Pharmacol Physiol. 2000; 27(7):558-62). Usually, drugs contained in eye drops are adsorbed by the corneal and the conjunctiva route; however, the solubility of the drugs and their inability to pass the barriers limits their effectiveness. Challenges for topical delivery to the retina include: poor adherence with ocular surface; low (<5%) bioavailability; loss due to lacrymal drainage; lack of blood supply to the cornea; isolated location; and protections from sclera, cornea, and retina. (Ilka R, Mohseni M, Kianirad M, Naseripour M, Ashtari K, Mehravi B. Nanogel-based natural polymers as smart carriers for the controlled delivery of Timolol Maleate through the cornea for glaucoma. International journal of biological macromolecules. 2018; 109:955-62).

To overcome these challenges, several polymeric and lipid-based nanomaterials are under intense investigation for eye delivery of genes and drugs. Nanoparticles ("NPs") designed to overcome these barriers can increase the drug and gene delivery to the retina. Multifunctional NPs with high targeting capability can ensure high transfection efficiency and drug accumulation. Dendrimers have been well established as nanodrug and gene delivery vehicles. (Lajunen T, Nurmi R, Kontturi L, Viitala L, Yliperttula M, Murtomaki L, Urtti A. Light activated liposomes: Functionality and prospects in ocular drug delivery. Journal of controlled release: official journal of the Controlled Release Society. 2016; 244(Pt B):157-66; Puglia C, Offerta A, Carbone C, Bonina F, Pignatello R, Puglisi G. Lipid nanocarriers (LNC) and their applications in ocular drug delivery. Curr Med Chem. 2015; 22(13):1589-602; Holden C A, Tyagi P, Thakur A, Kadam R, Jadhav G, Kompella U B, Yang H. Polyamidoamine dendrimer hydrogel for enhanced delivery of antiglaucoma drugs. Nanomedicine: nanotechnology, biology, and medicine. 2012; 8(5):776-83; Attama A A, Reichl S, Muller-Goymann C C. Sustained release and permeation of timolol from surface-modified solid lipid nanoparticles through bioengineered human cornea. Curr Eye Res. 2009; 34(8):698-705; Sahoo S K, Dilnawaz F, Krishnakumar S. Nanotechnology in ocular drug delivery. Drug Discov Today. 2008; 13(3-4):144-51; Motwani S K, Chopra S, Talegaonkar S, Kohli K, Ahmad F J, Khar R K. Chitosan-sodium alginate nanoparticles as submicroscopic reservoirs for ocular delivery: formulation, optimisation and in vitro characterisation. Eur J Pharm Biopharm. 2008; 68(3):513-25; Kutlehria S, Vhora I, Bagde A, Chowdhury N, Behl G, Patel K, Singh M. Tacrolimus Loaded PEG-Cholecalciferol Based Micelles for Treatment of Ocular Inflammation. Pharmaceutical research. 2018; 35(6):117; Sharma A, Anumanthan G, Reyes M, Chen H, Brubaker J W, Siddiqui S, Gupta S, Rieger F G, Mohan RR. Epigenetic Modification Prevents Excessive Wound Healing and Scar Formation After Glaucoma Filtration Surgery. Invest Ophthalmol Vis Sci. 2016; 57(7):3381-9; Tandon A, Sharma A, Rodier J T, Klibanov A M, Rieger F G, Mohan R R. BMP7 gene transfer via gold nanoparticles into stroma inhibits corneal fibrosis in vivo. PloS one. 2013; 8(6):e66434; Kadam R S, Williams J, Tyagi P, Edelhauser H F, Kompella U B. Suprachoroidal delivery in a rabbit ex vivo eye model: influence of drug properties, regional differences in delivery, and comparison with intravitreal and intracameral routes. Mol Vis. 2013; 19:1198-210).

Dendrimers are defined as nano-sized, radially symmetric molecules having a well-defined, homogenous and monodisperse structure. Dendrimers typically are comprised of a symmetric core, an inner shell composed of several building blocks and an outer shell comprised of different functional groups. (Abbasi, R. et al., Dendrimers: synthesis, applications and properties, Nanoscale Research Letters, 2014; 9(1):247-257). Dendrimers are synthesized from branched monomers of the type $AB_x$ where x>2. The monomers are layered around a core to construct an onion-like structure with each layer being termed a generation. The synthesis can be conducted from the core outwards, termed the divergent method, or from the end groups inward, termed the convergent method. Several types of dendrimers can be synthesized including, but not limited to, Poly(propyleneimine) dendrimers (PPI), Poly(amidoamine) dendrimers (PAMAM), Poly 2,2-bis(methylol)propionic acid (PBisMPA), Poly(benzyl ether) dendrimers (PBzE), poly(lysine) dendrimers (PLL) and polymelamine (triazine) dendrimers. (Bussy, e. et al., Chapter 16—Therapeutic Applications, Adverse Effects of Engineered Nanomaterials, 2012, pages 296-301).

Whereas dendrimers have been used for gene delivery to the posterior segment of the eye, topical formulations of the same are limited. (Palmerston Mendes L, Pan J, Torchilin V P. Dendrimers as Nanocarriers for Nucleic Acid and Drug Delivery in Cancer Therapy. Molecules. 2017; 22(9); Somani S, Blatchford D R, Millington O, Stevenson M L, Dufes C. Transferrin-bearing polypropylenimine dendrimer for targeted gene delivery to the brain. Journal of controlled release: official journal of the Controlled Release Society. 2014; 188:78-86; Biswas S, Torchilin V P. Dendrimers for siRNA Delivery. Pharmaceuticals (Basel). 2013; 6(2):161-83; Soto-Castro D, Cruz-Morales J A, Ramirez Apan M T, Guadarrama P. Solubilization and anticancer-activity enhancement of Methotrexate by novel dendrimeric nanodevices synthesized in one-step reaction. Bioorg Chem. 2012; 41-42:13-21; Duncan R, Izzo L. Dendrimer biocompatibility and toxicity. Advanced drug delivery reviews. 2005; 57(15): 2215-37; Pescina S, Ostacolo C, Gomez-Monterrey I M, Sala M, Bertamino A, Sonvico F, Padula C, Santi P, Bianchera A, Nicoli S. Cell penetrating peptides in ocular drug delivery: State of the art. Journal of controlled release: official journal of the Controlled Release Society. 2018; 284:84-102). Certain investigators have used dendrimers along with penetration enhancers, such as penetratin. However, the results have been controversial and off-target effects have been a concern. (Tai L, Liu C, Jiang K, Chen X, Feng L, Pan W, Wei G, Lu W. A novel penetratin-modified complex for noninvasive intraocular delivery of antisense oligonucleotides. Int J Pharm. 2017; 529(1-2):347-56; Tai L, Liu C, Jiang K, Chen X, Wei G, Lu W, Pan W. Noninvasive delivery of oligonucleotide by penetratin-modified polyplexes to inhibit protein expression of intraocular tumor. Nanomedicine: nanotechnology, biology, and medicine. 2017; 13(6):2091-100; Liu C, Jiang K, Tai L, Liu Y, Wei G, Lu W, Pan W. Facile Noninvasive Retinal Gene Delivery Enabled by Penetratin. ACS Appl Mater Interfaces. 2016; 8(30):19256-67).

Topical administration of therapeutic agents to treat the posterior segment of the eye are rarely used due to the lack of exposure to the retina. Only about 5% of a topically applied ophthalmic preparation may enter the posterior segment of the eye as the majority of the dose is systemically absorbed through the conjunctiva and nasal fluids and inner ocular tissues as well as lacrimal drainage. Drug delivery to the posterior segment of the eye is limited in part by the multiple physical boundaries within the eye, such as the corneal and conjunctival epithelium, blood aqueous barriers (BAB), and blood retinal barriers (BRB). These physical boundaries restrict passage of molecules and fluids to the retina and impede drug penetration. Due to these physical barriers, topical therapeutic agents such as eye drops, suspensions and ointments mainly target the anterior segment of the eye. (Jiang S. et al., Nanotechnology in retinal drug delivery, International Journal of Ophthalmology, 2018; 11(6):1038-1044). For effective systemic delivery, a relatively high drug concentration must circulate in the plasma in order to achieve a therapeutic dose in the eye, which is not optimal. Currently, drugs and genes are administered to the posterior eye by invasive intravitreal injections, which cannot be repeated too often.

Accordingly, what is needed is a nanoformulation(s) that can be delivered non-invasively and topically, leading to drug availability in the posterior eye and may be useful for many eye diseases. However, in view of the art considered as a whole at the time the present invention was made, it was not obvious to those of ordinary skill in the field of this invention how the shortcomings of the prior art could be overcome.

SUMMARY OF THE INVENTION

The long-standing but heretofore unfulfilled need for a nanoformulation and a non-invasive and topical method of delivery that leads to drug availability in the posterior eye is now met by a new, useful, and nonobvious invention.

An object of the invention is to provide a topical, non-invasive, and effective drug and gene formulation and delivery method for the posterior eye, which may be useful in treating many eye diseases without the need for invasive, expensive, and difficult-to-repeat procedures.

Toward developing a non-invasive topical approach to deliver therapeutic agents, such as DNA-based drugs and small molecules to the posterior eye, the inventors developed the topical multifunctional dendrimer nanoparticle (tMDN) platform. In this platform, dendrimers are surface functionalized to target the delivery of short hairpin RNAs (shRNAs) and small molecules to the retina. Generally, a functionalized polyamidoamine dendrimer is formed by complexation with a small molecule drug encapsulated cyclodextrin for increased solubility, as well as a short-hairpin RNA-encoding DNA molecule complexed to the surface of the polyamidoamine dendrimer.

In an embodiment, a drug delivery system for delivering a drug to a posterior segment of an eye of a patient is presented comprising: at least one polyamidoamine (PAMAM) dendrimer nanoparticle complexed with at least one short hairpin RNA (shRNA)-encoding DNA molecule and conjugated to cyclodextrin encapsulating a small molecule drug on an outer surface of the at least one PAMAM dendrimer nanoparticle and a pharmaceutically acceptable carrier. The at least one shRNA-encoding DNA molecule may be a dual expressing short hairpin RNA (shRNA) recombinant plasmid with the ratio of dendrimer to DNA being 1:5 by weight. G4 PAMAM may be used to construct the at least one PAMAM dendrimer nanoparticle.

The drug delivery system may further comprise a targeting agent conjugated to the outer surface of the at least one PAMAM dendrimer nanoparticle. The targeting agent may be hyaluronic acid, cholera toxin B domain, arginylglycylaspartic acid (RGD) peptide, or Tat peptide and may be used to target the CD44 receptor.

The drug delivery system may further comprise polyethylene glycol (PEG) conjugated to the outer surface of the at least one PAMAM dendrimer nanoparticle.

In another embodiment, a method of treating a disease of an eye of a patient in need thereof is presented comprising: providing at least one multi-functional PAMAM dendrimer nanoparticle comprising at least one polyamidoamine (PAMAM) dendrimer nanoparticle complexed with at least one short hairpin RNA (shRNA)-encoding DNA molecule and conjugated to cyclodextrin encapsulating a small molecule drug on an outer surface of the at least one PAMAM dendrimer nanoparticle; and suspending the at least one multi-functional PAMAM dendrimer nanoparticle in a pharmaceutically acceptable carrier to form a composition; and topically administering the composition to an eye of the patient wherein the composition targets the posterior segment of the eye of the patient.

The at least one multifunctional PAMAM dendrimer may further comprise a targeting agent conjugated to the outer surface of the at least one PAMAM dendrimer nanoparticle. The targeting agent may be hyaluronic acid, cholera toxin B domain, arginylglycylaspartic acid (RGD) peptide, or Tat peptide and may be used to target the CD44 receptor.

The at least one multifunctional PAMAM dendrimer may further comprise polyethylene glycol (PEG) conjugated to the outer surface of the at least one PAMAM dendrimer nanoparticle.

In a further embodiment, a method of delivering a therapeutic agent to a posterior segment of an eye of a patient in need thereof is presented comprising: providing a composition comprised of a pharmaceutically acceptable carrier and at least one multi-functional PAMAM dendrimer nanoparticle and topically administering the composition to the patient. The at least one multifunctional PAMAM dendrimer nanoparticle is comprised of at least one polyamidoamine (PAMAM) dendrimer nanoparticle having at least one short hairpin RNA (shRNA)-encoding DNA molecule, at least one cyclodextrin encapsulating a therapeutic agent, and at least one targeting agent complexed to an outer surface of the at least one PAMAM dendrimer nanoparticle. The at least one shRNA-encoding DNA molecule may be a dual expressing short hairpin RNA (shRNA) recombinant plasmid. G4 PAMAM may be used to construct the at least one PAMAM dendrimer nanoparticle. The therapeutic agent may be a small molecule drug.

The at least one multifunctional PAMAM dendrimer may further comprise a targeting agent conjugated to the outer surface of the at least one PAMAM dendrimer nanoparticle. The targeting agent may be hyaluronic acid, cholera toxin B domain, arginylglycylaspartic acid (RGD) peptide, or Tat peptide and may be used to target the CD44 receptor.

The at least one multifunctional PAMAM dendrimer may further comprise polyethylene glycol (PEG) conjugated to the outer surface of the at least one PAMAM dendrimer nanoparticle.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
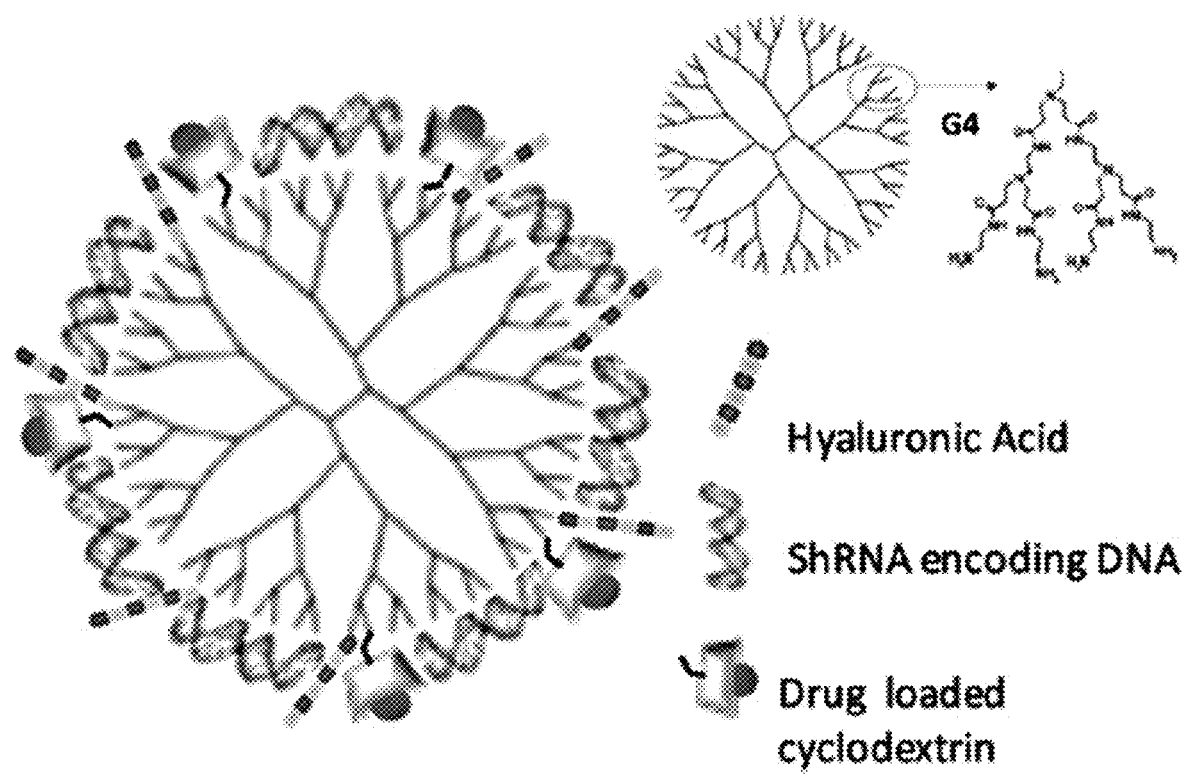
FIG. 1 is a schematic for the synthesis of multifunctional dendrimer nanoparticles ("MDNs") for retinal delivery.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose. As used herein the term "about" refers to within ±10% of the numerical.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used in this specification and the appended claims, the singular forms "a," "an," and "the" include plural referents unless the content clearly dictates otherwise. For example, the term "a nanoparticle" includes a plurality of nanoparticles, including mixtures thereof.

As used in this specification and the appended claims, the term "or" is generally employed in its sense including "and/or" unless the context clearly dictates otherwise.

The term "pharmaceutically active agent" as used herein refers to a molecule, a group of molecules, a complex or substance that is administered to a subject for diagnostic, therapeutic, preventative, medical, or veterinary purposes and includes drugs and vaccines. Included are externally and internally administered topical, localized and systemic human and animal pharmaceuticals, treatments, remedies, nutraceuticals, cosmeceuticals, biologicals, and diagnostics, including preparations useful in clinical and veterinary screening, prevention, prophylaxis, healing, wellness, detection, imaging, diagnosis, therapy, surgery, monitoring, cosmetics, forensics, and the like. The pharmaceutically active agents are preferably lipophilic for encapsulation within the nanoparticles of the present invention.

"Patient" is used to describe a vertebrate animal, preferably a mammal, more preferably a human, to whom treatment is administered, including prophylactic treatment with the compositions of the present invention. Vertebrate animals include mammals such as humans, primates, canines, felines, bovines, porcines, equines, ayes, ruminants, etc. The terms "patient" and "subject" are used interchangeably herein.

"Treatment" or "treating" as used herein refers to any of: the alleviation, amelioration, elimination and/or stabilization of a symptom, as well as delay in progression of a symptom of a particular disorder or disease. For example, "treatment" of an ocular disorder may include any one or more of the following: amelioration and/or elimination of one or more symptoms associated with ocular disease, reduction of one or more symptoms of ocular disease, stabilization of symptoms of ocular disease, and delay in progression of one or more symptoms of an ocular disease/disorder.

The "therapeutically effective amount" for purposes herein is thus determined by such considerations as are known in the art. A therapeutically effective amount of the drug delivery system, nanoparticles, pharmaceutically active agent, small molecule drug, gene or any combination thereof is that amount necessary to provide a therapeutically effective result in vivo. The amount must be effective to achieve a response, including but not limited to total prevention of (e.g., protection against) and to improved survival rate or more rapid recovery, or improvement or elimination of symptoms associated with ocular diseases and disorders or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Administration" or "administering" is used to describe the process in which the drug delivery system, nanoparticles, therapeutic agent, small molecule drug, gene or any combination thereof of the present invention are delivered to a patient. The composition may be administered in various ways including topically, among others.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once per day, at least once every other day, at least 3 times per week, at least twice per week, and at least once per week. In some embodiments, the interval between each administration is less than about 24 hours, such as less than about any of 23, 22, 21, 20, 19, 18, 17, 16, 15, 14, 13, 12, 11, 10, 9, 8, 7, 6, 5, 4, 3, 2, or 1 hour. In some embodiments, the interval between each administration is constant. For example, the administration can be carried out every hour, every two hours, every three hours, every four hours, every 5 hours, every six hours, every seven hours, every eight hours, every nine hours, every ten hours, every eleven hours, or every twelve hours. In some embodiments, the administration can be carried out twice daily, three times daily, or more frequent.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compounds used in the present invention may be administered individually, or in combination with or concurrently with one or more other compounds. Additionally, compounds used in the present invention may be administered in combination with or concurrently with other therapeutics for ocular disorders.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention and are capable of topical administration in the eye. Examples include, but are not limited to, phosphate buffered saline, physiological saline, water, and gels. Formulations are described in a number of sources that are well known and readily available to those skilled in the art. For example, *Remington's Pharmaceutical Sciences* (Martin E W [1995] Easton Pa., Mack Publishing Company, 19th ed.) describes formulations which can be used in connection with the subject invention.

For ease of administration, the subject compounds may be formulated into various pharmaceutical forms. As appropriate compositions there may be cited all compositions usually employed for topically administering drugs. For topical administration, the ophthalmic preparations may in the form of solutions, suspensions, ointments, gels or emulsions.

The term "DNA sequence" as used herein refers to both single stranded and double stranded DNA. The specific sequence, unless the context indicates otherwise, refers to the single strand DNA of such sequence, the duplex of such sequence with its complement (double stranded DNA) and the complement of such sequence.

The term "coding region" as used herein refers to that portion of a gene which either naturally or normally codes for the expression product of that gene in its natural genomic environment, i.e. the region coding in vivo for the native expression product of the gene. The coding region can be from a normal, mutated, or altered gene or a DNA sequence or gene wholly synthesized in the laboratory using methods well known to those of ordinary skill in the art.

The term "expression product" as used herein refers to the polypeptide or protein that is the natural translation product of the gene and any nucleic acid sequence coding equivalents resulting from genetic code degeneracy and thus coding for the same amino acid(s).

"Dendrimer" as used herein refers to a highly branched synthetic polymer macromolecules capable of being used in delivery of therapeutic agents, such as drugs, in a patient. Dendrimers are constructed by the successive addition of branching group layers with each branching group layer being a new generation. Dendrimers capable of being used herein include, but are not limited to, Poly(propyleneimine) dendrimers (PPI), Poly(amidoamine) dendrimers (PA-MAM), Poly 2,2-bis(methylol)propionic acid (PBisMPA), Poly(benzyl ether) dendrimers (PBzE), poly(lysine) dendrimers (PLL), and polymelamine (triazine) dendrimers. If PAMAM dendrimers are used, any of generations 0-11 (G0-G11) may be used. In some embodiments, PAMAM G4 is used. PAMAM dendrimers generally comprise an ethylenediamine core, a repetitive branching amidoamine internal structure and a primary amine terminal surface.

"Targeting agent" as used herein refers to an agent that specifically targets surface receptors on the retina. Examples of targeting agents include, but are not limited to hyaluronic acid, cholera toxin B domain, RGD peptide, and Tat peptide. In some embodiments, the surface receptor is CD44 and the targeting agent is hyaluronic acid.

"Multifunctional dendrimer nanoparticles" as used herein refers to dendrimers that have been functionalized by the complexation of various targeting agents, therapeutic agents and/or genes to deliver genes and/or therapeutic agents such as small molecule drugs to the posterior segment of the eye. In some embodiments, the dendrimers have a therapeutic agent such as a small molecule drug, such as pioglitazone, encapsulated in a complexing agent, such as cyclodextrin, complexed to the outer surface of the dendrimer. An shRNA encoding DNA plasmid may also be complexed to the outer surface of the dendrimer. In some embodiments, a targeting agent, such as hyaluronic acid is also complexed to the outer surface of the dendrimer.

"Therapeutic agent" as used herein refers to agents used to treat a posterior segment eye disease including, but not limited to, monoclonal antibodies, fusion proteins, genes, gene products, and small molecule drugs. Therapeutic agents may also be referred to as ophthalmic or ocular agents.

"Small molecule drug (SMD)" as used herein refers to a therapeutic agent that is a low molecular weight organic compound able to enter cells easily to affect a biological process including affecting biological targets such as proteins, enzymes, channels or receptors. Small molecule drugs generally have a size less than 900 Daltons.

"Posterior segment eye diseases" as used herein refers to diseases affecting the posterior segment of the eye. The posterior segment of the eye is defined as the portion of the eye that is behind the lens. This portion is comprised of the back ⅔ of the eye and is generally comprised of the retina and the vitreous body. Posterior segment eye diseases include, but are not limited to, glaucoma, age-related macular degeneration (ARMD), diabetic retinopathy (DR), cytomegalovirus (CMV) retinitis, proliferative vitreoretinopathy, Stargardt disease, retinoblastoma, and uveitis in the posterior of the eye.

"Functionalized" as used herein refers to altering the surface of the dendrimer by physical interactions or chemical conjugation with specific molecules to induce a desired bioresponse or inhibit a potentially adverse reaction while maintaining the functionality of both the dendrimer and the biomolecule. In some embodiments, the dendrimer surface is altered by conjugating or complexing drug-containing cyclodextrin, targeting agent, and shRNA encoding DNA to the surface of the dendrimer. The drug-containing cyclodextrin may be conjugated to available $NH_2$ groups. The shRNA encoding DNA may be contained within a plasmid which is complexed to the dendrimer surface.

"Complexing agent" as used herein refers to agents capable of being complexed to dendrimers to improve the bioavailability or stability of a small molecule drug. In some embodiments, the complexing agent may be used to increase aqueous solubility of poorly soluble drugs and to increase their bioavailability and stability. An exemplary complexing agent is cyclodextrin. Cyclodextrin can be natural and modified with natural cyclodextrin consisting of 6, 7, or 8 glucopyranose units, referred to as alpha, beta or gamma, respectively. Complexing agents may be used to encapsulate a therapeutic agent such as a small molecule drug.

The inventors have developed a functionalized polyamidoamine ("PAMAM") dendrimer for the effective delivery of shRNA-encoding DNA in combination with a small molecule drug such as pioglitazone (PG) encapsulated cyclodextrin. PAMAM dendrimer was selected for its good physicochemical properties and its ability to facilitate endosomal escape through its internal secondary and tertiary amines the so called "proton sponge" effect. While a specific PAMAM dendrimer is used herein, the invention contemplates use of other types of dendrimers and nanoparticles. The inventors demonstrate a novel dendrimer-based noninvasive topical approach using modified PAMAM dendrimer-based nanoparticles to deliver drugs and/or genes to the posterior eye.

Example 1—Construction of Multi-shRNA Vector pSH plasmid (Addgene), a mammalian expression vector that contains three sites for the insertion of DNA inserts is used for cloning DNAs expressing their short-hairpin RNAs. pSH utilizes the Human Ubiquitin C promoter for the transcription of a single mRNA transcript that is post-modified to express a maximum of three shRNAs and enhanced green fluorescence protein (EGFP) for fluorescent detection. Thus, an in-silico analysis of the desired genes is performed (Wizard 3.1, In Vivo Gen) followed by NCBI's BLAST to identify the shRNA sequences (19-24 bps). The oligos are synthesized by Integrated DNA Technologies (IDT) and cloned, using common lab methods. The cloned fragments are verified by Sanger sequencing and their silencing for gene function is evaluated in HEK293 transfected cells expressing these genes.

Example 2—Synthesis of Multifunctional Retina-Targeted Dendrimeric Nanoformulations FIG. 1 depicts a schematic of the multifunctional dendrimer-based nanoparticle (MDN). The MDN is a functionalized poly-amidoamine PAMAM dendrimer for the effective delivery of shRNA-encoding DNA in combination with small molecule drug (SMD)-encapsulated cyclodextrin.

PAMAM dendrimers were obtained from Dendritech® Inc. PAMAM dendrimer G4 was selected for its good physicochemical properties and its ability to facilitate endosomal escape through its internal secondary and tertiary amines, the so-called "proton sponge" effect. G4 PAMAM is selected because: (i) it is hyperbranched with 64 $NH_2$ ends for multifunctionalization, and (ii) it has been proven safer than G6 and G7 and is more effective than G3. The inventors functionalized the PAMAM dendrimers for the effective delivery of shRNA-encoding DNA in combination with small molecule drug(s) encapsulated cyclodextrin. G4 PAMAM dendrimers were modified by removing the bigger particles and aggregates using molecular extrusion to obtain a uniform size of ~10 nm. While G4 PAMAM was selected for use, any of PAMAM G0-G11 are contemplated for use in the present invention.

To develop the MDNs, a plasmid expressing shRNAs, such as a pSH plasmid, was selected to silence the desired gene(s) as described in Example 1. The plasmid was complexed with the PAMAM dendrimers. The pSH plasmid is a mammalian expression vector having three sites for DNA inserts via restriction digestion and subsequent ligation and comes with enhanced green fluorescence protein (EGFP) selection marker for fluorescent detection. Complex formation of PAMAM dendrimer with DNA at an optimal ratio of 1:5 (dendrimer:DNA) by weight changes the size to ~70 nm.

The PAMAM dendrimer was also conjugated with natural cyclodextrins. These natural cyclodextrins presumably enable fast disruption of the endosome, having shown higher (up to ~100-fold) gene expression in cells. After the complexation of the monotosyl-cyclodextrin with SMD, the complex is conjugated on the $NH_2$-groups on the surface of the dendrimer.

SMDs that are poorly soluble having a very low dissolution rate, which limits their pharmacodynamic activity and therapeutic action, can be complexed with cyclodextrins, including β- and γ-cyclodextrin, which not only increases the water solubility of lipophilic drugs and enhances their absorption into the eye but also reduces local irritation. Another advantage of the use of cyclodextrins on the proposed nanosystem is that dendrimer conjugates with natural cyclodextrins have shown higher gene expression in cells. The higher transfection efficiency was attributed to the fast disruption of the endosome caused by cyclodextrins. The density of cyclodextrins on the surface of the dendrimer can be optimized in order to achieve the higher SMD loading that ensures the therapeutic outcome. If the loading efficiency is low, then free SMDs are also loaded on the core of the dendrimer.

While the inventors conducted experiments using a pioglitazone (PG) loaded cyclodextrin, any small molecule drug (SMD) capable of being loaded into the complexing agent may be used in the instant invention. PG salts are poorly soluble and have a very low dissolution rate, which limits their pharmacodynamic activity and therapeutic action. β- and γ-cyclodextrin are commonly used in ophthalmology to increase the water solubility of PG and enhance its absorption into the eye and reduce local irritation. As such, while any of the cyclodextrins may be used in the instant invention, either β- or γ-cyclodextrin are preferred as the complexing agent.

The surfaces of the proposed MDNs are further functionalized with hyaluronic acid to target the CD44 receptor, which is overexpressed on retina pigment epithelial cells. Another advantage of the hyaluronic acid (HA) outer coating is that the strong negative charge on the surface increases the stability of the formulation and its overall effectiveness. To ensure the accumulation of NPs to the retina, in lieu of HA, other targeting agents such as the Cholera toxin B domain, RGD peptide and/or Tat peptide can be conjugated on the nanoparticle surface. (Tandon 2013; Kadam 2013)

In order to improve the colloidal stability of the proposed nanosystem, the PAMAM dendrimer surface is shielded with NHS-PEG-methoxy conjugated through its NHS ester group to the remaining PAMAM amine groups.

Example 3—Characterization of MDNs

MDNs are characterized for their physicochemical properties, such as size and charge, using dynamic light scatter analyses and zeta sizers, as described.

Figure 2:
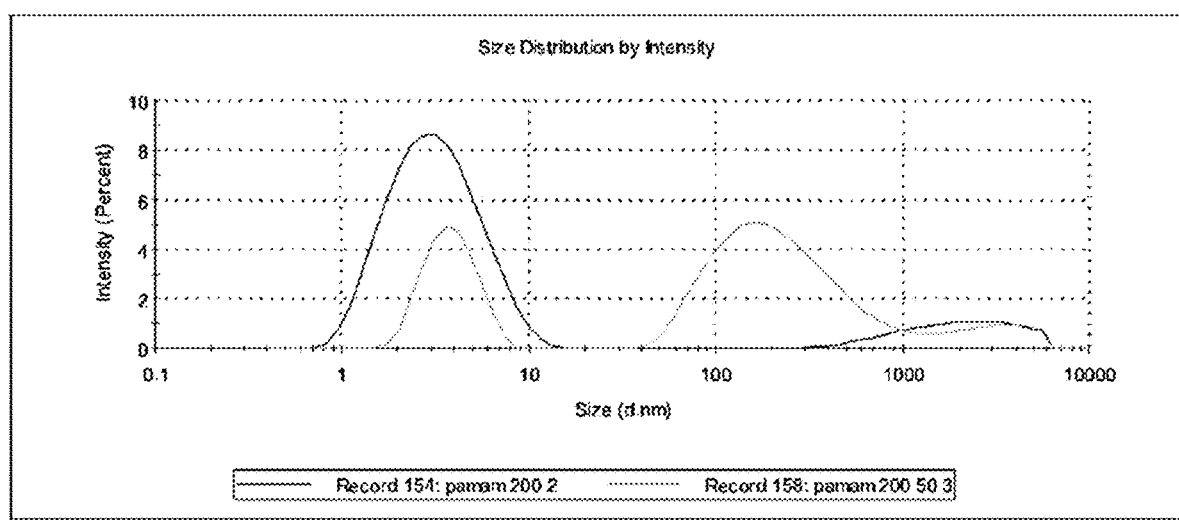
FIG. 2 is a graph depicting a size distribution analysis of G4-PAMAM dendrimers by dynamic light scattering ("DLS").

As shown in FIG. 2, the average size of the PAMAM-$NH_2$ dendrimer is 25 nm, but there are two separated peaks, one peak at 5 nm and one peak at 200 nm (light grey line). 50 nm monodispersed particles were obtained after extrusion using 50 nm pore size membranes (light grey line).

Figure 3:
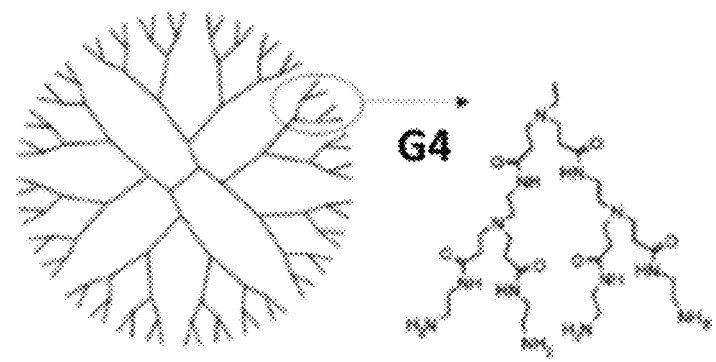
FIG. 3 is an image depicting a conjugation and characterization of OPSS-PEG-NHS to —$NH_2$ groups on the surface of the dendrimer of FIG. 2.
Figure 3:
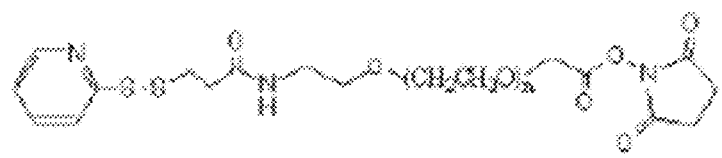
Figure 3:
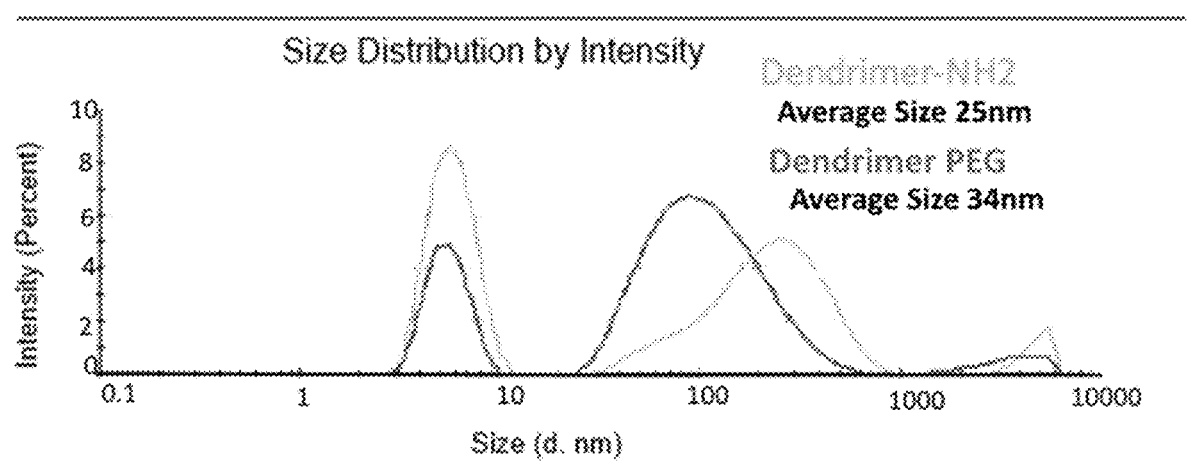

As shown in FIG. 3, to increase functionalization of dendrimers, G4-PAMAM was conjugated to the 2-pyridinethione end, which can be used for the redox responsive conjugation of any thiolated ligand, while the PEG will increase the stability and protect the pDNA complexed on the surface of NPs. OPSS-PEG-NHS was conjugated to —$NH_2$ groups on the surface of the dendrimer. TNBSA assay was used for the estimation of free amine groups before and after OPSS-PEG-NHS conjugation. The conjugation yield was 95%. The average size before and after PEG conjugation was 25 nm and 34 nm, respectively.

Figure 4A:
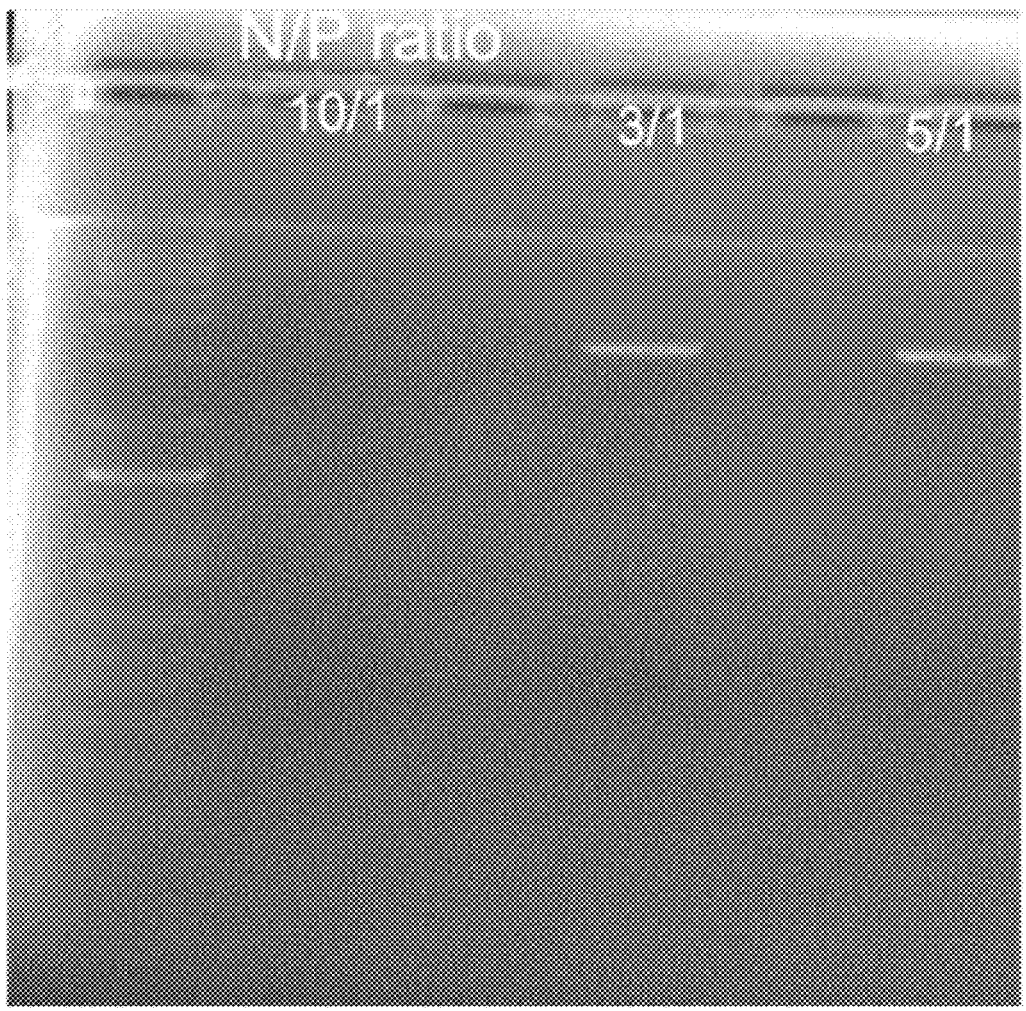
FIG. 4A depicts a DNA encapsulation and characterization of DNA binding with dendrimers, particularly showing a gel electrophoresis of complexes with differing N:P ratios.
Figure 4B:
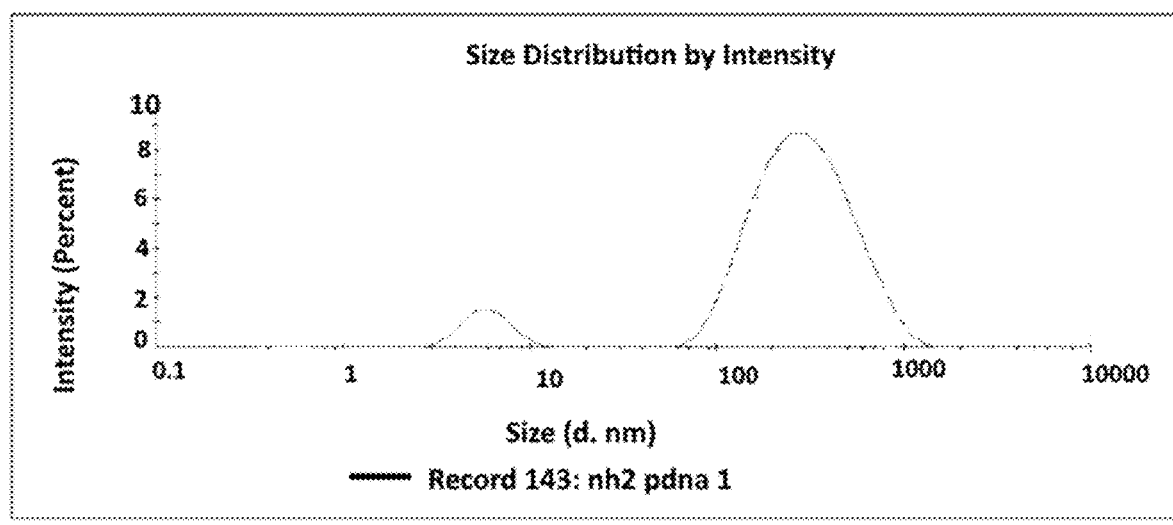
FIG. 4B depicts a DNA encapsulation and characterization of DNA binding with dendrimers, particularly a graph depicting a size distribution analysis by DLS of complexes.

As shown in FIGS. 4A and 4B, a new Dendrimer-$NH_2$/pCMV-tdTomato sample was prepared using the monodispersed particles, and the final size was found to be less than 50 nm. Agarose gel electrophoresis was used to assess the formation of Dendrimer-$NH_2$/pCMV-tdTomato complexes at different ratios. NP size after pDNA conjugation increased to 130 nm. A 5:1 ratio (DNA:dendrimer) by weight was found to be optimal.

Figure 5A:
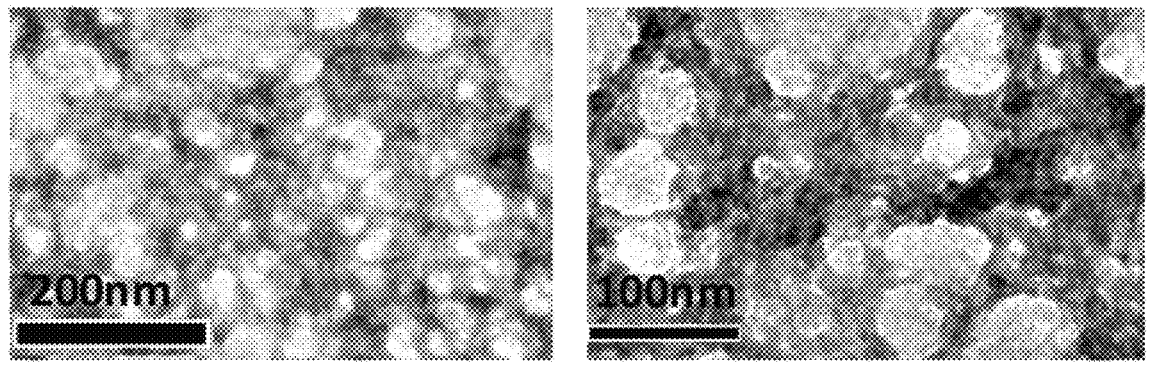
FIG. 5A is a transmission electron microscopy ("TEM") image of PAMAM dendrimers complexed with 0.2 µg/µL of tdTomato plasmid DNA.
Figure 5B:
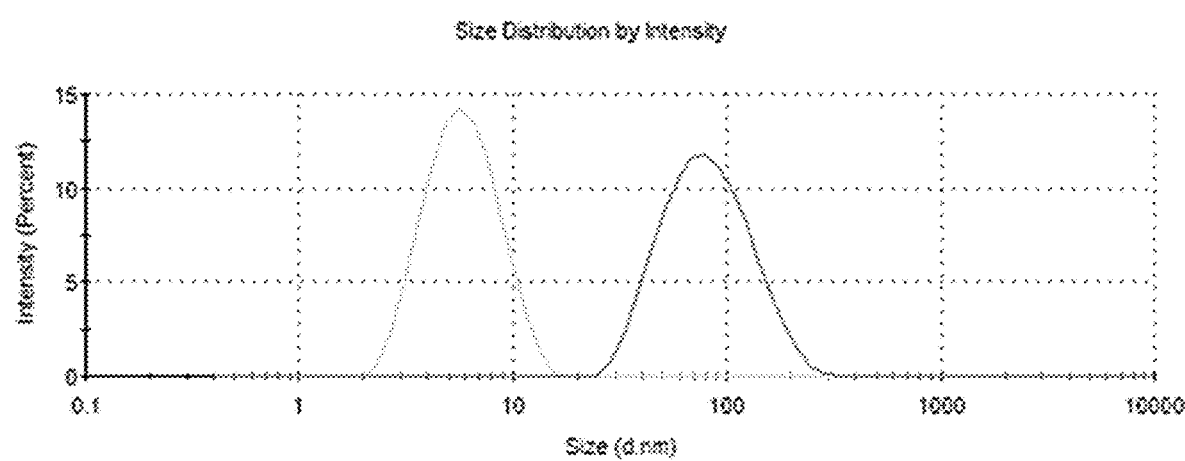
FIG. 5B is a graph depicting a size distribution analysis of PAMAM dendrimers complexed with 0.2 µg/µL of tdTomato plasmid DNA.
Figure 5C:
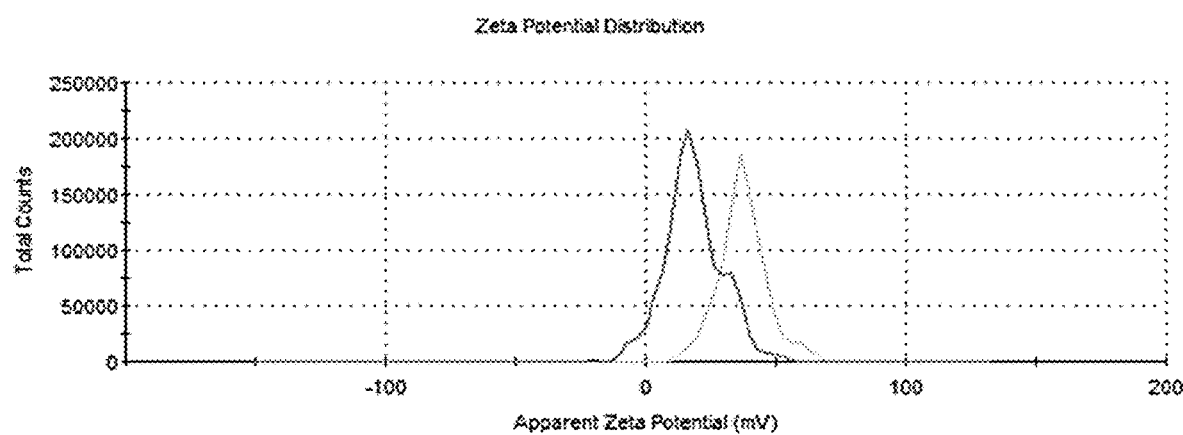
FIG. 5C is a graph depicting zeta potential of PAMAM dendrimers complexed with 0.2 µg/µL of tdTomato plasmid DNA.

As shown in FIGS. 5A-C, the resulting dendrimer-based NPs from each step of the synthesis procedure was characterized and found to represent the expected physiochemical properties. Each NP was characterized based upon the final size, zeta-potential, and visual appearance obtained via TEM. Size (shown in FIG. 5B) and zeta-potential (shown in FIG. 5C) were measured with Malvern DLS.

Example 4—In Vitro Studies

Cell uptake and safety of MDNs are examined in vitro using murine brain microglia cells, BV-2, and human retinal epithelial cells, ARPE-19. The efficacy of MDNs to reduce desired gene expression is evaluated in CCL20/CCR6 transfected HEK293 cells.

Example 5—In Vivo Studies

In vivo drug release profile and ocular distribution of MDNs was evaluated in C57BL/6 mice. Briefly, eyes of C57BL/6 mice (N=10/group) are treated with MDN carrying varying doses of shRNA plasmid as an ocular drop (5 µL drops, 3× per day). One eye of the mouse receives 5 µL of MDNs while the other eye receives 5 µL of PBS. To evaluate the gene expression in vivo, the eyes are collected 48 and 72 hours after the first instillation and examined for GFP expression. Also, ocular distribution of MDNs (EGFP expression) is examined using Micron IV Retinal Fundus Imaging Microscope (Phoenix Research Labs).

Figure 6:
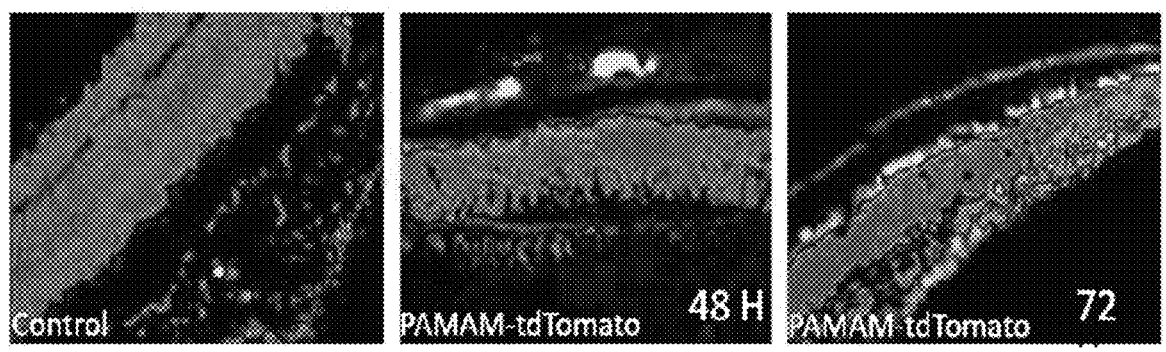
FIG. 6 depicts retinal RFP expression. BALB/c mice were administered topically, as eye drops, 5 µL per eye, three times per day. The left eye received PBS, and the right eye received multifunctional dendrimer nanoparticles ("MDNs"). The eyes were sectioned 48 hours and 72 hours post-administration and examined for RFP expression after each section.

As shown in FIG. 6, the eyes of BALB/c mice were treated with 0.2 µg/µL of tdTomato plasmid using simple instillation of 5 µL drops per eye, three times per day. The right eyes received PAMAM dendrimers while the left eyes 5 µL of PBS. To evaluate the gene expression in vivo, the eyes were collected 48 and 72 hours after the first instillation and examined for RFP expression. Topically applied MDNs resulted in expression of RFP in the posterior eye including retinal epithelium, as shown in FIG. 6, suggesting these MDNs do reach retinal epithelium and retinal cells.

Example 6—Prophetic Example

A male diabetic patient is diagnosed with retinal neuropathy. The patient was unable to tolerate intravitreal injection and was referred for topical treatment with multifunctional dendrimer nanoparticles. The patient is treated with a therapeutically effective amount of the drug delivery system composition comprised of multifunctional dendrimer nanoparticles suspended in a pharmaceutically acceptable carrier. The composition is formulated as an eye drop for topical administration in the eye. The MDNs have shRNA encoding DNA in a plasmid complexed to the surface of the MDNs. Pioglitazone (PG) loaded cyclodextrin and hyaluronic acid as a targeting agent are also complexed to the surface of the dendrimer. The composition is administered topically to the infected eyes at a therapeutically effective dosage at regular intervals. Improvement in vision is seen after a time period.

CONCLUSION

The inventors have developed a novel multifunctional dendrimer nanoparticle (MDN) capable of being topically delivered to treat diseases of the posterior segment of the eye. The MDNs are PAMAM dendrimers having various functional groups complexed to the surface including shRNA encoding DNA plasmids, small molecule drug encapsulated cyclodextrins and targeting agents such as hyaluronic acid. The MDNs described herein are able to be administered topically and can target the posterior segment of the eye, specifically the retina. The MDNs are a noninvasive alternative to current therapies for treatment of posterior segment eye diseases.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween. Now that the invention has been described,

What is claimed is:

1. A drug delivery system for delivering a drug to a posterior segment of an eye of a patient comprising:
   a multifunctional dendrimer-based nanoparticle (MDN) comprising
      at least one modified polyamidoamine (PAMAM) dendrimer nanoparticle modified by using molecular extrusion to remove large particles and aggregates to obtain a size of about 10 nm;
      at least one short hairpin RNA (shRNA)-encoding DNA molecule complexed to an outer surface of the at least one modified PAMAM dendrimer nanoparticle;
      at least one natural cyclodextrin encapsulating pioglitazone on the outer surface of the at least one modified PAMAM dendrimer nanoparticle; and
      a targeting agent targeting a CD44 receptor conjugated to the outer surface of the at least one modified PAMAM dendrimer nanoparticle wherein the targeting agent is selected from the group consisting of hyaluronic acid, cholera toxin B domain, arginylglycylaspartic acid (RGD) peptide, and Tat peptide; and
   a pharmaceutically acceptable carrier.

2. The drug delivery system of claim 1, wherein the natural cyclodextrin is β- or γ-clclodextrin.

3. The drug delivery system of claim 1, further comprising polyethylene glycol (PEG) conjugated to the outer surface of the at least one PAMAM dendrimer nanoparticle.

4. The drug delivery system of claim 1, wherein the at least one shRNA-encoding DNA molecule is a dual expressing short hairpin RNA (shRNA) recombinant plasmid.

5. The drug delivery system of claim 1, wherein the PAMAM is G4 PAMAM.

6. The drug delivery system of claim 1, wherein the ratio of dendrimer to DNA is 1:5.

* * * * *